United States Patent [19]
Wong et al.

[11] Patent Number: 5,391,381
[45] Date of Patent: * Feb. 21, 1995

[54] DISPENSER CAPABLE OF DELIVERING PLURALITY OF DRUG UNITS

[75] Inventors: Patrick S. L. Wong, Palo Alto; Felix Theeuwes, Los Altos Hills; James B. Eckenhoff, Los Altos; Steven D. Larsen, Dublin; Hoa T. Huynh, Union City, all of Calif.

[73] Assignee: ALZA Corporation, Palo Alto, Calif.

[ * ] Notice: The portion of the term of this patent subsequent to Jun. 11, 2008 has been disclaimed.

[21] Appl. No.: 60,372

[22] Filed: May 11, 1993

Related U.S. Application Data

[63] Continuation-in-part of Ser. No. 873,901, Apr. 24, 1992, Pat. No. 5,236,689, which is a continuation-in-part of Ser. No. 701,927, May 17, 1991, Pat. No. 5,110,597, which is a continuation of Ser. No. 495,825, Mar. 19, 1990, Pat. No. 5,023,088, which is a continuation-in-part of Ser. No. 283,772, Dec. 13, 1988, abandoned, which is a continuation-in-part of Ser. No. 270,730, Nov. 14, 1988, abandoned, which is a continuation-in-part of Ser. No. 66,905, Jun. 25, 1987, abandoned.

[51] Int. Cl.$^6$ ............................................. A61K 9/24
[52] U.S. Cl. ..................................... 424/473; 424/472; 604/892.1
[58] Field of Search ........................ 424/473; 604/892.1

[56] References Cited

U.S. PATENT DOCUMENTS

| | | | |
|---|---|---|---|
| 3,133,132 | 5/1964 | Loeb et al. | 264/49 |
| 3,173,876 | 3/1965 | Zobrist | 242/137 |
| 3,276,586 | 10/1966 | Rosaen | 210/90 |
| 3,541,005 | 11/1970 | Strathmann et al. | 210/19 |
| 3,541,006 | 11/1970 | Bixler et al. | 210/23 |
| 3,546,142 | 12/1970 | Michaels et al. | 260/2.1 |
| 3,845,770 | 11/1974 | Theeuwes et al. | 128/130 |
| 3,865,108 | 2/1975 | Hartop | 128/260 |
| 3,916,899 | 11/1975 | Theeuwes et al. | 128/260 |
| 3,995,631 | 12/1976 | Higuchi et al. | 128/260 |
| 4,002,173 | 1/1977 | Manning et al. | 128/296 |
| 4,034,756 | 7/1977 | Higuchi et al. | 128/260 |
| 4,077,407 | 3/1978 | Theeuwes et al. | 128/260 |
| 4,111,202 | 9/1978 | Theeuwes | 128/260 |
| 4,160,020 | 7/1979 | Ayer et al. | 424/15 |
| 4,203,441 | 5/1980 | Theeuwes | 128/260 |
| 4,207,893 | 6/1980 | Michaels | 128/260 |
| 4,220,152 | 9/1980 | Dresback | 128/260 |
| 4,320,759 | 3/1982 | Theeuwes | 128/260 |
| 4,327,725 | 5/1982 | Cortese et al. | 128/260 |
| 4,350,271 | 9/1982 | Eckenhoff | 222/386.5 |
| 4,449,983 | 5/1984 | Cortese et al. | 604/892 |
| 4,526,938 | 7/1985 | Churchill et al. | 525/415 |
| 5,034,229 | 7/1991 | Magruder et al. | 424/422 |

Primary Examiner—D. Gabrielle Phelan
Attorney, Agent, or Firm—Paul L. Sabatine; Jacqueline S. Larson; Alisa A. Harbin

[57] ABSTRACT

A dispenser for use in a fluid environment which is capable of delivery of a plurality of discrete drug-containing units in any desired delivery pattern or profile.

21 Claims, 5 Drawing Sheets

DISPENSER CAPABLE OF DELIVERING PLURALITY OF DRUG UNITS

RELATED PATENT APPLICATIONS

This application is a continuation-in-part of application Ser. No. 07/873,901, filed Apr. 24, 1992, now U.S. Pat. No. 5,236,687, which is a continuation-in-part of application Ser. No. 07/701,927, filed May 17, 1991, now U.S. Pat. No. 5,110,597, which is a continuation of 07/495,825, filed Mar. 19, 1990, now U.S. Pat. No. 5,023,088, which is a continuation-in-part of application Ser. No. 07/283,772, filed Dec. 13, 1988, abandoned, which is a continuation-in-part of application Ser. No. 07/270,730, filed on Nov. 14, 1988, abandoned, which is a continuation-in-part of application Ser. No. 07/066,905, filed Jun. 25, 1987, abandoned, which applications are assigned to ALZA Corporation and are incorporated herein by reference, and benefit is claimed of their filing dates.

This application is related to the coassigned U.S. Pat. Nos. 4,874,388 and 4,957,494.

FIELD OF THE INVENTION

This invention relates to patterned drug delivery. More particularly, this invention relates to patterned drug delivery by means of a plurality of individual drug delivery units or tablets. Still more particularly, but without limitation thereto, this invention relates to delivery of agents orally or in other media in a preprogrammed delivery profile.

BACKGROUND OF THE INVENTION

The concept of patterned drug delivery covers a broad range of systems from time-release capsules whose components have coatings which erode at different rates, to controlled release rate tablets which operate by osmosis.

Despite the development of the art, however, there remains a continuing need for improved methods and systems for providing controlled drug release profiles.

SUMMARY OF THE INVENTION

An object of this invention is to provide sequential timing and dispensing of dosage units containing the same or different active agents.

Another object of this invention is to provide sequential timing and dispensing of two dosage units simultaneously, the units containing the same or different active agents.

Yet another object of this invention is to provide both a novel and a useful agent formulation delivery system that is self-contained, self-powered, and also represents an improvement in the delivery art.

A further object of the invention is to provide clean and quick delivery of sequential pulses of active agent to an environment of use having a relatively low fluid content.

These and other objects are demonstrated by the present invention wherein an active agent dispenser for use in a fluid-containing environment comprises a rigid housing, a plurality of movable active agent units and, optionally, non-active agent units filling a portion of the housing, a fluid-activated driving member for dispensing the active agent units filling the remainder of the housing and an active agent unit outlet means.

BRIEF DESCRIPTION OF THE DRAWINGS

The invention will be described in further detail with reference to the accompanying drawings wherein.

DETAILED DESCRIPTION OF THE INVENTION AND OF THE PREFERRED EMBODIMENTS

Figure 1:
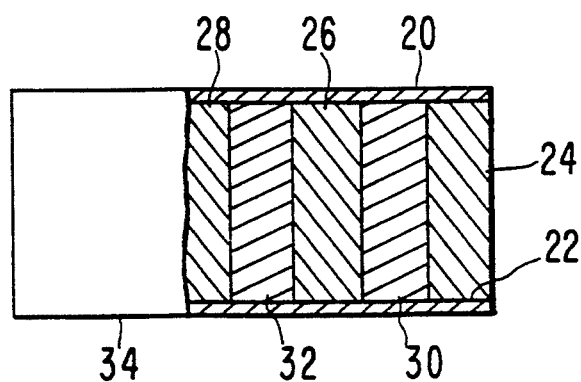
FIG. 1 is a partial cross-sectional view of the dispenser of this invention, illustrating one embodiment of the dispensing configuration.

This invention can provide a variety of drug delivery profiles including, but not limited to, pulsed delivery of a single drug or drug formulation, pulsed delivery of a sequence of different drugs or drug formulations, pulsed delivery of one drug or drug formulation superimposed on continuous delivery of a different drug or drug formulation, pulsed delivery of two drugs or drug formulations simultaneously, and simultaneous continuous delivery of several drugs or drug formulations.

The expressions "active agent" and "drug" are used interchangeably and as used herein broadly include any compound, composition of matter or mixture thereof that can be delivered from the system to produce a beneficial and useful result. This includes pesticides, herbicides, germicides, biocides, algicides, antivirals, rodenticides, fungicides, insecticides, anti-oxidants, plant growth promoters, plant growth inhibitors, preservatives, anti-preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators and other agents that benefit the environment of use.

The terms "active agent" and "drug" as used herein further include any physiologically or pharmacologically active substance that produces a localized or systemic effect or effects in animals, including warm-blooded mammals, humans and primates; avians; domestic household, sport or farm animals such as dogs, sheep, goats, cattle, horses and pigs; laboratory animals such as mice, rats and guinea pigs; fish; reptiles; zoo and wild animals. The active drug which can be delivered includes inorganic and organic compounds, including, without limitation, those materials that act upon the central nervous system such as hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetrics, diuretics, lipid regulating agents, antiandrogenic agents, antiparasitics, neoplastics, antineoplastics, hypoglycemics, nutritional agents, fats, ophthalmics, electrolytes and diagnostic agents.

This invention is particularly suited to the delivery of pharmacologically active peptides and protein anabolic hormones such as growth promoting hormones related to the endocrine system comprising, for example, porcine growth promoting hormone, bovine growth promoting hormone, equine growth promoting hormone, ovine growth promoting hormone, human growth promoting hormone, growth promoting hormones derived by extraction and concentration from pituitary and hypothalamus glands, growth promoting hormones produced by recombinant DNA methods, bovine growth promoting hormone as described in Nucleic Acid Res., Vol. 10, p 7197 (1982), ovine growth. promoting hormone as described in Arch. Biochem. Biophys., Vol. 156, p 493 (1973), and porcine growth promoting hormone as described in DNA, Vol. 2, pp 37, 45 (1983). Also included are polypeptides such as growth hormone, somatropin, somatotropin, somatomedin-C, gonadotropic releasing hormone, follicle stimulating hormone, luteinizing hormone, LH-RH, growth hormone releasing factor, gonadotropin releasing factor, insulin, colchicine, chorionic gonadotropin, oxytocin, vasopressin, adrenocorticotrophic hormone, epidermal growth factor, prolactin, somatostatin, cosyntropin, lypressin, polypeptides such as thyrotropin releasing hormone, thyroid stimulating hormone, secretin, pancreozymin, enkephalin, glucagon, and the like. The active agents and their dosage unit amounts are known to the art in *The Pharmacological Basis of Therapeutics*, by Gilman, Goodman, Rall and Murad, 7th Ed. (1985), published by MacMillan Publishing Co., N.Y.; in *Pharmaceutical Sciences*, Remington, 17th Ed. (1985), published by Mack Publishing Co., Easton, Pa.; and in U.S. Pat. No. 4,526,938.

It is to be understood that more than one active agent may be incorporated into the active agent formulation in a device of this invention, and that the use of the term "agent" or "drug" in no way excludes the use of two or more such agents or drugs. The agents can be in various forms, such as uncharged molecules, components of molecular complexes or nonirritating, pharmacologically acceptable salts. Also, simple derivatives of the agents (such as ethers, esters, amides, etc.) which are easily hydrolyzed by body pH, enzymes, etc., can be employed.

The term "active agent formulation" as used herein comprises the active agent or drug to be delivered, as a liquid, solid, semisolid or thermosensitive composition, generally in a carrier substance and with or without additional inert ingredients. The term additionally includes an active agent or drug in the form of active agent dosage forms.

The terms "drug unit," "dosage unit," "active agent unit" and "active agent dosage unit" as used herein include units that are capable of maintaining their physical configuration and chemical integrity while housed within the dispenser. This includes, without limitation, tablets with or without a density element; matrix tablets; pellets and elongated tablets where the height-to-diameter ratio exceeds one; capsules; elementary osmotic pumps, such as that described in U.S. Pat. No. 3,845,770; mini-osmotic pumps, such as those described in U.S. Pat. Nos. 3,995,631, 4,034,756 and 4,111,202; and multichamber osmotic systems referred to as push-pull and push-melt osmotic pumps, such as those described in U.S. Pat. Nos. 4,320,759 and 4,449,983; all of which are incorporated herein by reference.

As used herein, the expression "external fluid" includes water and other biological fluids.

As used herein, the terms "therapeutically effective" amount or rate refer to the amount or rate of the active agent needed to effect the desired therapeutical, often beneficial, result.

The drug delivery system or dispenser of this invention is designed to deliver a plurality of discrete longitudinally aligned individual drug units by the linear expansion of a fluid-activated driving member. The drug units are such that they retain their physical and chemical integrity while contained within the system and do not substantially commence delivery of active agent until after they have been dispensed into the environment. The dispenser is comprised of a dispensing component and a driving component, representative embodiments of which are disclosed herein. FIGS. 1, 2, 3 and 8 illustrate various embodiments of the dispensing component suitable for use in the dispenser of this invention. These configurations can be combined with various embodiments of the driving component, representative embodiments of which are illustrated in FIGS. 4–7, and of the housing structure itself, shown in FIGS. 1, 4, 6, 9–13 and 15. The drug delivery system or dispenser of this invention may, alternately, be comprised of a driving component and two dispensing components, a representative embodiment of which is illustrated in FIG. 14.

The dispensing and driving component designs are for use in a fluid-containing environment and are merely exemplary of the numerous embodiments suitable for use in this invention. The portion of the housing adjacent to the dispenser component is of a material which may be either semipermeable or substantially impermeable to the passage of external fluid. Typical suitable impermeable materials include, without limitation, polyethylene, compressed polyethylene fine powder, polyethylene terephthalate (Mylar ®), plasticized polyvinyl chloride, metal-foil polyethylene laminates, neoprene rubber, natural gum rubber and Pliofilm ®(rubber hydrochloride). These materials are additionally flexible, insoluble and chemically compatible with the active agent contained in the units positioned therein, and, in the instance of providing a drug or like depot within the body of a living organism, are biologically inert, non-irritating to body tissues and non-allergenic. Additional suitable materials include polystyrene, polypropylene, polyvinyl chloride, reinforced epoxy resin, polymethylmethacrylate, etc., sheet metal (e.g., aluminum, copper, steel, etc.), galvanized pipe, or styrene/acrylonitrile copolymer. Again, for drug depot applications the same are advantageously biologically inert, non-irritating to body tissue and non-allergenic. Suitable semipermeable materials include, without limitation, all cellulosic polymers such as cellulose acetates, ethyl cellulose, methyl cellulose, cellulose acetate butyrate, cellulose acetate propionate, etc., or impermeable material blended with a hydrophilic polymer or a low molecular weight water-soluble enhancer to render the material semipermeable.

Many other materials including those which are biologically acceptable are suitable for fabrication of the impermeable component of the device of this invention. While the impermeable portion of the housing has previously been described as being insoluble under the conditions and in the environment of intended use, it is also within the scope of the invention that such materials be insoluble only during the period of said intended use, thereafter dissolving or otherwise degrading into the environment of the device. Thus, a dispenser is here contemplated which is unaffected by its environment, solubility-wise, at the situs of use, or which is only slightly soluble during the period of intended use, such that once all the units have been dispensed, it will then dissolve or erode away, leaving no objectionable residue or empty container at the said situs of use.

The portion of the housing adjacent to the driving component must be semipermeable so as to allow for passage of external fluid, since the driving member is fluid-activated. Suitable materials will be discussed at length with regards to specific embodiments of the driving member.

The dispensing component shown in FIG. 1 is comprised of a rigid housing member 20. Housing 20 is also designed with an outlet means, exit port 22. A plurality of movable discrete units 24, 26, 28, 30 and 32 are aligned within the housing 20. This configuration is merely illustrative, and the dispenser may have numerous drug units other than the number shown in FIG. 1.

The drug units are in the form of a solid core or a matrix tablet or in any of a variety of forms which are capable of maintaining their physical and chemical integrity, i.e. do not substantially erode while in the housing. The driving member 34 operates to displace the units towards the exit port 22. As unit 24 comes into contact with the exit, it is dispensed into the environment and begins to deliver drug in a controlled or semicontrolled fashion. Once unit 24 is dispensed, linear displacement pushes unit 30 through the housing 20 so that it then comes into contact with exit 22 and is likewise dispensed. This continues until the dispenser is depleted of drug units.

The units can provide a variety of drug delivery profiles depending upon their composition. They can all contain the same drug(s) at the same concentration(s) to deliver identical pulses of drug over time as each unit is dispensed, or they can contain the same drug(s) at different concentrations to give different pulses of drug. Alternately, the units may contain different drugs or drug formulations.

The drug units of this invention may also contain binders, lubricants, and, optionally, excipients such as compounds to stabilize the drug or to facilitate erosion. An example of a suitable composition as contemplated by this invention is about 60–95 wt % drug, about 2–3 wt % binder, about 0.1–5 wt % lubricant, about 1–20 wt % excipient to facilitate disintegration or erosion and about 1–10 wt % excipient to stabilize the drug.

Materials suited for use in formulating the drug units of this invention are well known in the art and are fully described in texts such as *Pharmaceutical Sciences*, Remington, Chapter 87 (supra). Binders which impart cohesive qualities include, without limitation, starch, gelatin, agar, natural and synthetic gums, carboxycellulose, carboxymethylcellulose, methylcellulose, hydroxypropylmethylcellulose, polyvinyl alcohol, polyvinylpyrrolidone, polyethylene glycol, cellulose acetate, polyurethane and waxes. Lubricants serve numerous purposes including improving the rate of flow of the granulated particles and facilitating the actual manufacture of the units. Suitable lubricants include, without limitation, talc, starch, zinc stearate, aluminum stearate, magnesium stearate, calcium stearate, boric acid, sodium chloride, paraffin, stearic acid, low melting point waxes, hydrogenated vegetable oils and saturated fatty acid esters. The units may also include a disintegrant such as lightly cross-linked polyvinylpyrrolidone, corn starch, potato starch, Veegum ®, bentonite and citrus pulp. It may also be desirable to include stabilizers for the drug. These include, without limitation, sodium bisulfite and histidine HCl.

The drug unit composition may also be modified to include about 0.1–5 wt % of a surfactant and/or about 0.01–2 wt % of an anti-oxidant, for example. Suitable surfactants include, without limitation, sorbitan monostearate, polysorbate 80 USP (polyoxyethylene (20) sorbitan monooleate), and polyoxyethylene 4 stearate. Suitable antioxidants include, without limitation, tertiary butyl-4-methoxyphenol (mixture of 2- and 3-isomers), 2,6-ditertiary butyl-p-cresol, propyl gallate, 6-ethoxy-1,2-dihydro-2,2,4-trimethylquinoline (ethoxyquin) and nordihydroguaiaretic acid (NDGA).

In a preferred embodiment, units 24, 26 and 28 contain a drug or drug formulation and alternate units 30 and 32 contain no drug, such that when they are dispensed, an "off" period is provided, during which time no drug is being delivered. The additional advantage of this "alternating" configuration is that once unit 24 is dispensed, the surface of unit 30 is exposed and may begin the erode. Having 30 as a non-drug-containing unit guarantees that the drug being delivered to the environment comes from the dispensed unit rather than from the units still retained within the housing.

Figure 2:
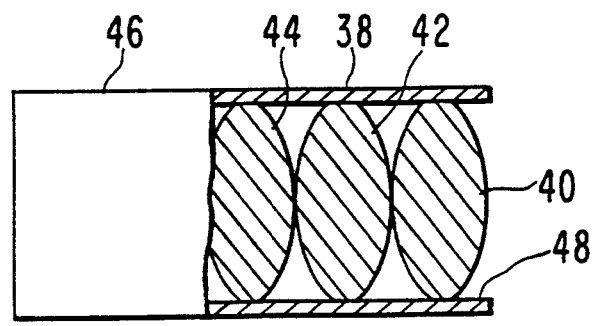
FIG. 2 is a partial cross-sectional view of the dispenser of this invention, illustrating a second embodiment of the dispensing configuration.

The dispensing configuration shown in FIG. 2 is also designed to deliver a plurality of discrete units to the environment, and operates similarly to the embodiment of FIG. 1. In FIG. 1, the geometry of the units permits close alignment so as not to have any space between adjacent units. This aspect is not critical to the effectiveness of the invention, as is shown by FIG. 2 where the units are curved and therefore do not fit closely together within the housing.

The dispensing configuration of FIG. 2 is comprised of a rigid housing 38 and a plurality of discrete drug units 40, 42 and 44, aligned therein. Three drug units are shown, but in actual application any number of units may be used. The driving member 46 displaces the units at the desired rate and dispenses them individually through the exit port 48. The drug units, 40 for example, can be elementary osmotic pumps or mini-osmotic pumps, for example. They can also be coated with a degradable coating to delay delivery until the units are actually dispensed into the environment.

Figure 3:
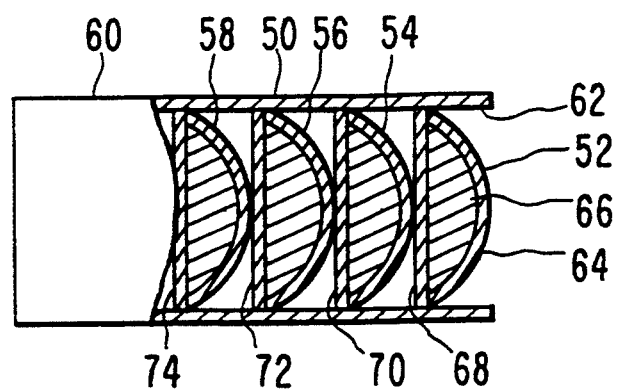
FIG. 3 is a partial cross-sectional view of the dispenser of this invention, illustrating still another embodiment of the dispensing configuration.

The dispensing configuration shown in FIG. 3 is comprised of a housing member 50 and a plurality of discrete drug units 52, 54, 56 and 58 aligned therein. As with FIGS. 1 and 2, the number of units shown is merely illustrative and is not intended to limit the invention in any manner.

The driving member 60 operates to linearly displace the units and dispense them through the exit port 62. The units, 52 for example, are comprised of a plastic or polyethylene cap 64 with a drug mixture 66 compressed within. The units may be bowl-shaped as shown or they may be box-shaped to hold a larger quantity of drug. The units are separated by partitions 68, 70, 72 and 74, which can be a rigid solid or a gel. As the unit 52 is dispensed, the drug mixture 66 is exposed to the environment (external fluid) and is thus delivered. Subsequently, the partition 68 is dispensed through the exit port 62.

This dispensing configuration provides pulsed drug delivery. As unit 52 is dispensed, a burst of drug is delivered which is followed by another pulse when unit 54 is dispensed and so forth. The units may contain the same drug in the same or different concentrations, or different drugs. In this manner, any pattern of delivery may be fashioned.

EXAMPLE I

The dispenser of FIG. 3 is especially suited for treatment of helminth infections in ruminants, specifically cattle. Depending upon the nature of delivery desired, several drug formulations can be used in this dispenser.

A suitable drug formulation is comprised of about 80 weight percent Hapadex ® which is an anthelmintic agent for cattle sold by Schering-Plough Corporation. About 0.5 grams of the formulation 66 is compressed into cap 64 to form unit 52. Units 54, 56 and 58 are also filled with the drug formulation. However, if an off period is desired, units 52 and 56 can contain drug and the alternate units 54 and 58 can be empty.

For fast pulse delivery of Hapadex ®, the drug formulation is 100% drug. However, this system can be designed to provide a short-duration pulse where the drug formulation has a gas generator contained therein. Especially suitable is a formulation comprised of about 80% Hapadex ® and about 20% citric acid/sodium bicarbonate.

If a longer period of delivery is desired, a disintegrating agent such as Ac-Di-Sol ® (FMC Corporation), otherwise known as croscarmellose sodium, can be incorporated into the drug formulation in an amount up to 20 weight percent.

For even longer duration of drug delivery, the drug formulation can be 80% Hapadex ® and 20% polymer, such as Polyox ® (polyethylene oxide polymers) or hydroxypropylmethylcellulose.

For ruminal systems, an important criteria is that the system remain in the rumen of an animal over a prolonged period of time. This is accomplished by placement of a density element within the dispenser. The housing 50 itself may be the density element. Alternately, one of the partitions, 74 for example, can act as the density element. In still another embodiment, unit 58 can be a density element, placed so as to remain within the housing 50 after all of the drug-containing units have been dispensed.

The density element suitable for use in the dispenser of this invention must be dense enough to retain the dispenser in the rumen-reticular sac of a ruminant. The presence of a density element allows the dispenser to remain in the rumen over a prolonged period of time rather than letting it pass into the alimentary tract and be eliminated therefrom. As the dispenser remains in the rumen, a beneficial agent can be delivered to the ruminant at a controlled rate over an extended period of time. Generally, a density element will have a density of from about 0.8 to 8, or higher, with the density in a presently preferred embodiment exhibiting a specific gravity of from about 2.2 to 7.6. For the ruminants cattle and sheep, it is presently preferred that the density element exhibit a density such that there is a resulting dispenser density of about 3. Materials that have a density that can be used for forming a suitable density element include iron, iron shot, iron shot coated with iron oxide, iron shot magnesium alloy, steel, stainless steel, copper oxide, a mixture of cobalt oxide and iron powder, and the like.

Exemplary of drugs that are soluble or very soluble in water and can be delivered by the dispenser systems of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, metacholine chloride, pilocarpine hydrochloride, atropine sulfate, methscopolamine bromide, isopropamide iodide, tridihexethyl chloride, phenformin hydrochloride, methylphenidate hydrochloride, histidine hydrochloride, copper sulfate, and mixtures thereof.

Exemplary of agents that have limited solubility or are very slightly soluble or insoluble in water and biological fluids and can be delivered by the dispenser systems of this invention include acyclovir, diphenidol, meclizine hydrochloride, prochlorperazine maleate, gemfibrozil, phenytoin, thiethylperazine maleate, anisindione, diphenadione, erythrityl tetranitrate, digoxin, isoflurophate, reserpine, azetazolamide, methazolamide, bendroflumethiazide, chlorpropamide, tolazamide, flutamide, nilutamide (anandron), chlormadinone acetate, phenaglycodol, allopurinol, aluminum aspirin, methotrexate, acetyl sulfisoxazol, erythromycin, and mixtures thereof, erythromycin ethyl succinate, steroids including corticosteroids such as hydrocortisone, hydrocorticosterone acetate, cortisone acetate and triamcinolone, anhydrogens such as methyltestosterone, esterogenic steroids such as 17-β-estradiol, ethinyl estradiol, ethinyl estradiol 3-methyl ether and estradiol, progestational steroids such as prednisolone, 17-α-hydroxyprogesterone acetate, 19-nor-progesterone, norethindrone, progesterone, gestodene, ST-1435 and norethynodrel, and the like.

The drug can also be in the various chemical and physical forms such as uncharged molecules, molecular complexes, and pharmacologically acceptable acid addition and base addition salts such as hydrochlorides, hydrobromides, sulfate, laurylate, palmitate, phosphate, nitrate, borate, acetate, maleate, tartrate, oleate and salicylate. For acidic drugs, salts of metals, amines or organic cations, for example quaternary ammonium, can be used. Derivatives of drugs such as esters, ethers and amides can be used alone or mixed with other drugs. Also, a drug which is water insoluble can be used in a form that, on its release from the dispenser, is converted by enzymes, hydrolyzed by body pH or other metabolic processes to the original form, or to a biologically active form.

The dispensing configuration of FIGS. 1, 2 and 3 can be combined with any of the driving members illustrated in FIGS. 4, 5, 6, and 7 to provide a tailored drug delivery system.

Figure 4:
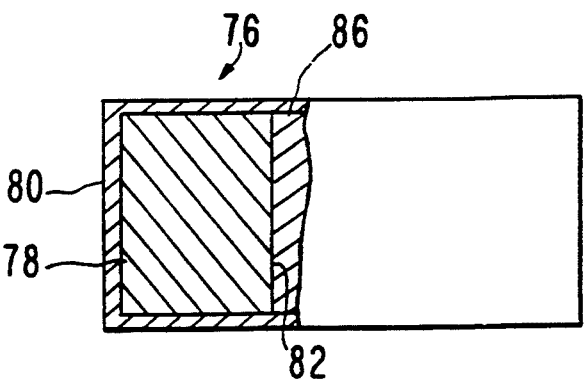
FIG. 4 is a partial cross-sectional view of one embodiment of the driving member for the dispenser of this invention, utilizing a hydrophilic expandable member.

FIG. 4 illustrates a driving member system 76 utilizing an expandable driving member 78 comprised of an external fluid-insoluble, external fluid-swellable composition. Member 78 is encased in housing 80 which is a semipermeable membrane substantially permeable to the passage of an external fluid and substantially impermeable to the passage of any ingredients contained in member 78. The driving member 78 is positioned adjacent to one of the drug units at interface 82.

External fluid is imbibed through the housing 80 by the expandable hydrophilic member 78 in a tendency toward osmotic equilibrium to continuously swell and expand member 78. Member 78 expands while maintaining an intact immiscible boundary at interface 82, defined by the surface of drug unit 86 and expandable member 78.

Expandable member 78 has a shape that corresponds to the internal shape of housing 80 and in one preferred embodiment is made from a hydrogel composition. The hydrogel composition is noncross-linked or optionally cross-linked and it possesses osmotic properties, such as the ability to imbibe an external fluid through semipermeable housing 80, and to exhibit an osmotic pressure gradient across semipermeable housing 80 against a fluid outside the dispenser system.

The materials used for forming the swellable expandable member 78 are polymeric materials neat and, in another preferred embodiment, polymeric materials blended with osmotic agents that interact with water or a biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2- to 50-fold volume increase. The swellable, hydrophilic polymers, also known as osmopolymers, can be noncross-linked or lightly cross-linked. The cross-links can be covalent, ionic or hydrogen bonds with the polymer possessing the ability to swell in the presence of fluid, and when cross-linked it will not dissolve in the fluid. The polymer can be of plant, animal, or synthetic origin. Polymeric materials useful for the present purpose include poly(hydroxyalkyl methacrylate) having a molecular weight of from 5,000 to 5,000,000; poly(vinyl pyrrolidone) having a molecular weight of from 10,000 to 360,000; anionic and cationic hydrogels; poly(electrolyte) complexes; poly(vinyl alcohol) having a low acetate residual; a swellable mixture of agar and carboxymethylcellulose; a swellable composition comprising methylcellulose mixed with a sparingly cross-linked agar; a water-swellable copolymer produced by a dispersion of finely divided copolymer of maleic anhydride with styrene, ethylene, propylene, or isobutylene; a water-swellable polymer of N-vinyl lactams; swellable sodium salts of carboxymethylcellulose; carboxyethylcellulose; carrageenans; alginates and sodium salts thereof; and the like.

Other gellable, fluid-imbibing and retaining polymers useful for forming the hydrophilic, expandable driving member 78 include pectin having a molecular weight ranging from 30,000 to 300,000; polysaccharides such as agar, acacia, karaya, tragacanth, algins and guar; Carbopol ® acidic carboxy polymer and its salt derivatives; polyacrylamides; water-swellable indene maleic anhydride polymers; Good-rite ® polyacrylic acid having a molecular weight of 80,000 to 200,000; Polyox ® polyethylene oxide polymers having a molecular weight of 100,000 to 5,000,000; starch graft copolymers; Aqua-Keep ® acrylate polymers with water absorbability of about 400 times its original weight; diesters of polyglucan; a mixture of cross-linked poly(vinyl alcohol) and poly(N-vinyl-2-pyrrolidone); poly(ethylene glycol) having a molecular weight of 4,000 to 100,000; and the like. In a preferred embodiment, the expandable member 78 is formed from polymers and polymeric compositions that are thermoformable.

Representative polymers possessing hydrophilic properties are known in U.S. Pat. Nos. 3,865,108, 4,002,173, 4,207,893, 4,220,152, 4,327,725, and 4,350,271, all of which are incorporated herein by reference, and in Scott et al, *Handbook of Common Polymers*, CRC Press, Cleveland, Ohio (1971).

The osmotically effective compound that can be blended homogeneously or heterogeneously with the swellable polymer to form a driving member is selected from the osmotically effective solutes that are soluble in fluid imbibed into the swellable polymer and exhibit an osmotic pressure gradient across the semipermeable housing 80 against an external fluid. Osmotically effective compounds are known also as osmagents. Osmotically effective osmagents useful for the present purpose include magnesium sulfate, magnesium chloride, sodium chloride, lithium chloride, potassium sulfate, sodium sulfate, mannitol, urea, sorbitol, inositol, sucrose, glucose and the like. The osmotic pressure in atmospheres (atm) of the osmagents suitable for the invention will be greater than zero atm, generally from 8 atm up to 500 atm, or higher.

Representative materials for forming the semipermeable housing include, without limitation, semipermeable homopolymers, semipermeable copolymers, and the like. In one embodiment, typical materials include cellulose esters, cellulose monoesters, cellulose diesters, cellulose triesters, cellulose ethers, and cellulose ester-ethers, mixtures thereof, and the like. These cellulose polymers have a degree of substitution (D.S.) on their anhydroglucose unit from greater than zero up to 3, inclusive. By "degree of substitution" is meant the average number of hydroxyl groups originally present on the anhydroglucose unit that are replaced by a substituting group or converted into another group. The anhydroglucose unit can be partially or completely substituted with groups such as acyl, alkanoyl, aroyl, alkyl, alkenyl, alkoxy, halogen, carboalkyl, alkylcarbamate, alkylcarbonate, alkylsulfonate, alkylsulfamate, and like semipermeable polymer forming groups.

The semipermeable materials typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di- and tri-alkenylates, mono-, di- and tri-aroylates, and the like. Exemplary polymers include cellulose acetate having a D.S. of 1.8 to 2.3 and an acetyl content of 32% to 39.9%; cellulose diacetate having a D.S. of 1 to 2 and an acetyl content of 21% to 35%; cellulose triacetate having a D.S. of 2 to 3 and an acetyl content of 34% to 44.8%; and the like. More specific cellulosic polymers include cellulose propionate having a D.S. of 1.8 and a propionyl content of 38.5%; cellulose acetate propionate having an acetyl content of 1.5% to 7% and a propionyl content of 39% to 42%; cellulose acetate propionate having an acetyl content of 2.5% to 3%, an average propionyl content of 39.2% to 45% and a hydroxyl content of 2.8% to 5.4%; cellulose acetate butyrate having a D.S. of 1.8, an acetyl content of 13% to 15%, and a butyryl content of 34% to 39%; cellulose acetate butyrate having an acetyl content of 2% to 29.5%, a butyryl content of 17% to 53%, and a hydroxyl content of 0.5% to 4.7%; cellulose triacylates having a D.S. of 2.9 to 3, such as cellulose trivalerate, cellulose trilaurate, cellulose tripalmitate, cellulose trioctanoate, and cellulose tripropionate; cellulose diesters having a D.S. of 2.2 to 2.6., such as cellulose disuccinate, cellulose dipalmitate, cellulose dioctanoate, and cellulose dicarpylate; cellulose propionate morpholinobutyrate; cellulose acetate butyrate; cellulose acetate phthalate; and the like; mixed cellulose esters, such as cellulose acetate valerate, cellulose acetate succinate, cellulose propionate succinate, cellulose acetate octanoate, cellulose valerate palmitate, cellulose acetate heptonate, and the like. Semipermeable polymers are known in U.S. Pat. No. 4,077,407, incorporated herein by reference, and they can be made by procedures described in *Encyclopedia of Polymer Science and Technology*, Vol. 3, pages 325-354, Interscience Publishers, Inc., New York (1964).

Additional semipermeable polymers include cellulose acetaldehyde; dimethylcellulose acetate; cellulose acetate ethylcarbamate; cellulose acetate methylcarbamate; cellulose dimethylaminoacetate; a cellulose composition comprising cellulose acetate and hydroxypropylmethylcellulose; a composition comprising cellulose acetate and polyethylene glycol; a composition comprising cellulose acetate and cellulose acetate butyrate; a composition comprising cellulose acetate butyrate and hydroxypropylmethylcellulose; semipermeable polyamides; semipermeable polyurethanes; semipermeable polysulfanes; semipermeable sulfonated polystyrenes; crosslinked, selectively semipermeable polymers formed by the coprecipitation of a polyanion and a polycation as disclosed in U.S. Pat. Nos. 3,173,876, 3,276,586, 3,541,005, 3,541,006 and 3,546,142, all of which are incorporated herein by reference; selectively semipermeable silicon rubbers; semipermeable polymers as disclosed by Loeb and Sourirajan in U.S. Pat. No. 3,133,132, incorporated herein by reference; semipermeable polystyrene derivatives; semipermeable (polysodiumstyrenesulfonate); semipermeable poly(-vinylbenzyltrimethyl) ammonium chloride; semipermeable polymers exhibiting a fluid permeability of $10^{-1}$ to $10^{-7}$ (cc.mil/cm$^2$ hr-atm) expressed as per atmosphere of hydrostatic or osmotic pressure difference across a semipermeable wall. The polymers are known to the art in U.S. Pat. Nos. 3,845,770, 3,916,899 and 4,160,020, all of which are incorporated herein by reference; and in J. R. Scott and W. J. Roff, *Handbook of Common Polymers*, CRC Press, Cleveland, Ohio (1971).

Other materials that can be used to form the semipermeable housing for imparting flexibility and elongation properties to the wall, for making the housing less- to non-brittle and to render tear strength, include phthalate plasticizers such as dibenzyl phthalate, dihexyl phthalate, butyl octyl phthalate, straight-chain phthalates of six to eleven carbons, diisononyl phthalate, diisodecyl phthalate, and the like. The plasticizers include nonphthalates such as citric acid esters, triacetin, dioctyl azelate, epoxidized tallate, triisoctyl trimellitate, triisononyl trimellitate, sucrose acetate isobutyrate, epoxidized soybean oil, and the like. The amount of plasticizer in the housing, incorporated therein, is about 0.01% to 20% by weight, or higher.

Figure 5:
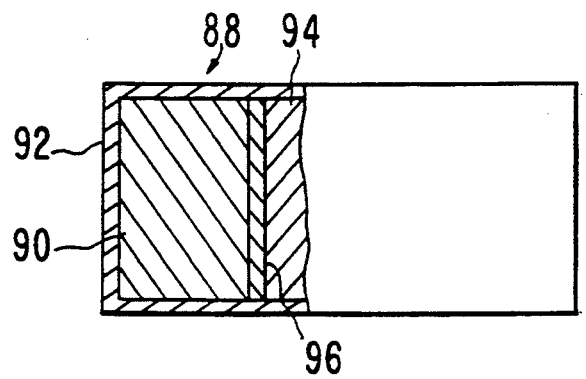
FIG. 5 is a partial cross-sectional view of a second embodiment of the driving member for the dispenser of this invention, utilizing an osmotically effective solute.

FIG. 5 illustrates a driving member 88 utilizing an osmotically effective solute. The osmotically effective solute is in solution 90 which is retained within a rigid housing 92 comprised of a semipermeable membrane substantially permeable to the passage of an external fluid and substantially impermeable to the passage of the osmotically effective solute contained in solution 90. The solution 90 is separated from the drug units, 94 for example, by means of a flexible membrane 96.

The ability of driving member 88 to displace the drug units, 94 for example, housed within a dispenser depends upon the osmotic pressure generated by the solution 90 of the osmotically effective solute confined within housing 92. This solution exhibits an osmotic pressure gradient against fluid in the environment into which the dispenser is placed, and is preferably a saturated aqueous salt solution. To maintain the solution saturated and therefore to achieve a constant osmotic pressure throughout operation of the dispenser, the housing containing the solution also contains excess solute in solid form. Various osmotically effective solutes can be used. These include magnesium sulfate, magnesium chloride, sodium chloride, potassium sulfate, sodium carbonate, sodium sulfite, sodium sulfate, sodium bicarbonate, potassium acid phthalate, calcium bicarbonate, potassium acid phosphate, raffinose, tartaric acid, succinic acid, calcium succinate, calcium lactate and magnesium succinate. The excess solid can be in the form of dispersed particles or preferably in the form of a pellet. The solution can initially be a solution of the same or of an osmotically effective solute different than the solid excess solute.

Figure 6:
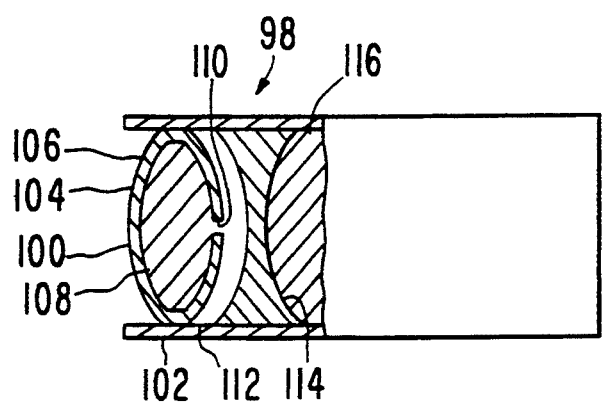
FIG. 6 is a partial cross-sectional view of another embodiment of the driving member for the dispenser of this invention, utilizing an elementary osmotic pump.

FIG. 6 illustrates a driving member 98 which is similar in operation to that of FIG. 5. An elementary osmotic pump 100, such as that disclosed in U.S. Pat. No. 3,845,770, is held rigidly in place in the impermeable housing 102, being exposed to the environment at surface 104. External fluid is imbibed through the semipermeable wall 106 by the osmotically effective solute 108 contained within the pump 100. As the osmotic pressure within the pump 100 increases, solution (external fluid and osmotic solute) is forced through the orifice 110 into chamber 112, thereby exerting pressure on piston 114 which subsequently moves through the housing 102 to dispense the drug units 116 contained therein. In order for this driving member to be operable, the wall of the housing 102 immediately surrounding the pump 100 must be impermeable to the passage of fluid so that external fluid does not enter chamber 112. Therefore, use of driving member 98 mandates that the housing be at least in part of an impermeable composition. In this manner, the housing in contact with the drug units can be semipermeable or impermeable.

Figure 7:
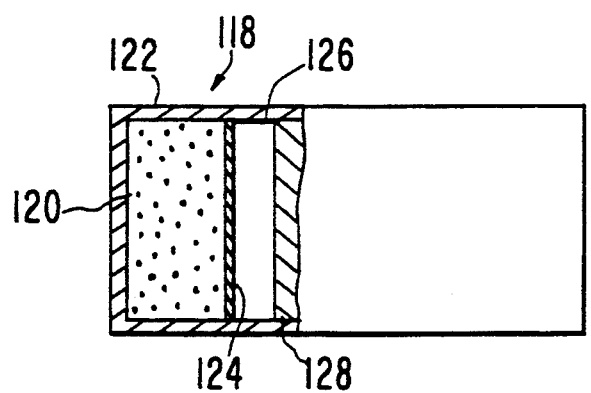
FIG. 7 is a partial cross-sectional view of another embodiment of the driving member for the dispenser of this invention, utilizing a gas-generating composition.

FIG. 7 illustrates a driving member 118 which operates by means of a gas-generating composition 120. Housing 122 is made of a semipermeable material which is substantially impermeable to the passage of gas-generating composition 120, has a low permeability to the passage of an internally generated gas and is substantially permeable to the passage of an external fluid. Membrane 124 is made of a semipermeable material which is substantially impermeable to the passage of gas-generating composition 120 and substantially permeable to the passage of a generated gas. Its main function is to keep the gas-generating composition 120 apart from the drug units contained in the dispenser.

In operation, external fluid is imbibed through housing 122 to continuously wet and dissolve the gas-generating composition 120, causing it to react and produce a large volume of gas. This gas expands and passes through membrane 124, filling the area 126. This action correspondingly causes pressure to be exerted on the drug unit 128 which thereby pushes this and the other units contained therein through the housing 122.

Gas-generating composition 120 consists essentially of a dry compound or an anhydrous mixture of compounds that, when intimately contacted by an external fluid that enters the housing 122, generates a gas that exerts a pressure to drive the dispensing system. The composition 120 comprises a preferably solid acidic material and a preferably solid basic material that dissolve and react in the presence of fluid that enters the housing 122. This composition may be in powder, crystalline, granular or layered form. Alternately, the gas-generating composition 120 may be present homogeneously or heterogeneously dispersed in a matrix. The matrix is a polymer permeable to the passage of external fluid and permeable to the passage of the generated gas. The rate of gas generated in this embodiment is governed by the rate of fluid passage through the polymer coupled with the rate of fluid passage through the housing 122. Suitable materials are disclosed in U.S. Pat. No. 4,203,441, incorporated herein by reference.

Figure 8:
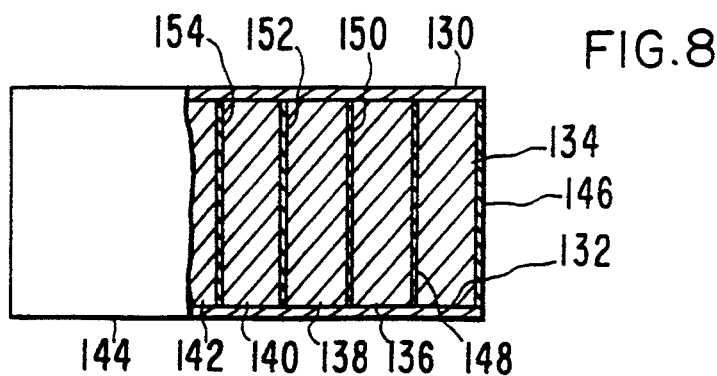
FIG. 8 is a partial cross-sectional view of the dispenser of this invention, illustrating another embodiment of the dispensing configuration.

Another embodiment of the dispensing configuration of this invention is illustrated in FIG. 8. This embodiment is especially suited for delivery of units which all contain drug, where it is desired to prevent delivery from units which are still contained within the housing. The dispenser of FIG. 8 is comprised of a rigid housing member 130 which is designed with an outlet means, exit port 132. A plurality of movable discrete units 134, 136, 138, 140 and 142 are aligned within the housing 130, and are displaced towards the exit port 132 by means of driving member 144. The drug units are similar in form to those described with reference to FIG. 1 but are all drug-containing units rather then drug-containing units alternating with non-drug-containing units.

In FIG. 8, while the units are contained within the housing they are protected from exposure to the environmental fluid by means of a plurality of plastic or polyethylene partitions 146, 148, 150, 152 and 154. When the dispenser is placed in the environment of use, the driving member 144 becomes fluid-activated and linearly displaces the units, first dispelling the partition 146 and then unit 134. As unit 134 is delivering drug, unit 136 is gradually being displaced towards the exit 132 and in the meantime is protected from the environment by partition 148.

FIGS. 9–13 illustrate examples of housing structures useful for use with this invention. These structures and suitable materials therefor are fully described in the coassigned U.S. Pat. No. 5,034,229, incorporated herein by reference. In general terms, the housing embodiments disclosed therein are described as having two walled sections, one substantially impermeable section which defines the dispensing component and one semipermeable section which defines the driving component. The driving component is typically an expandable material such as is described with reference to expandable member 78 in FIG. 4.

Figure 9:
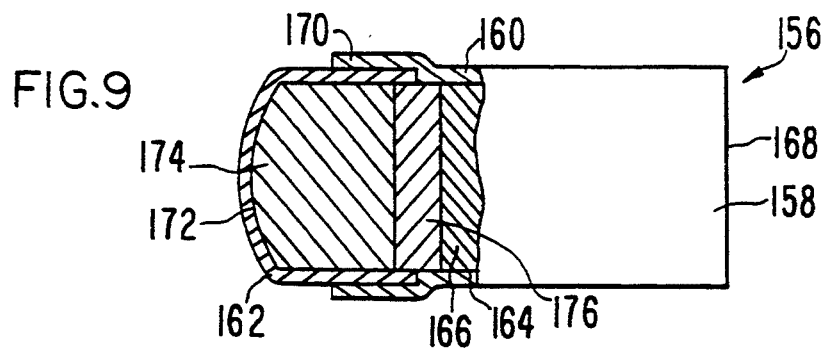
FIG. 9 is a partial cross-sectional view of an embodiment of the housing for the dispenser of this invention, having a first walled section and a second walled section.

FIG. 9 depicts a partial cross-sectional view of delivery system 156, which comprises housing member 158. Housing member 158 comprises a dispensing component identified by a first wall section 160 and a driving component identified by a second wall section 162, which surround and define internal compartment 164, which contains a plurality of drug units, 166 for example. Wall section 160 at its end distant from exit port 168 defines and forms receiving means 170. Receiving means 170 is enlarged slightly for receiving second wall section 162. Wall section 162 surrounds the internal compartment area 172 that contains driving component 174, which is suited for expanding and for occupying space in compartment 172 for delivery of a plurality of drug units from delivery system 156. The two wall sections, sections 160 and 162, at receiving end 170 are close in size and they form a tight friction fit therebetween. There is clearance or tolerance in size to allow wall section 162 a sliding movement into the receiving means 170 of wall section 160. Wall section 160 and wall section 162 can be telescoped completely into a closed and continuous walled position. Optionally, they can be held together by heat fusion, by an adhesive, or the like.

Wall section 160 comprises a composition that is substantially impermeable to the exchange of fluid, drug and other ingredients contained in the delivery system 156. Wall section 160, in a presently preferred manufacture, is substantially impermeable to the ingress of an external fluid to serve as a means for substantially protecting drug units that may contain a drug which is sensitive to fluid from an exterior fluid present in the environment of use. Wall section 160 substantially restricts and prevents fluid from passing through wall 160 and entering into compartment 164 in the region containing the drug units. Wall section 162 comprises in at least a part a semipermeable wall composition that is permeable to the passage of fluid for making fluid available to an expandable driving means 174 inside compartment 172. Wall section 162 is permeable to the passage of fluid and it is substantially impermeable to the passage of other ingredients contained in delivery system 156. Wall sections 160 and 162 optionally comprise a plasticizer that imparts flexibility and workability to the wall. Housing 158, comprising sections 160 and 162, is non-toxic and, in a presently preferred embodiment, it maintains its physical and chemical integrity, that is, housing 158 does not erode during the dispensing period.

Compartment 164 optionally comprises a layer 176, which is positioned between the drug layer 166 and the driving component 174. Layer 176, in a presently preferred embodiment, comprises a composition that is substantially impermeable to the passage of fluid and it serves to restrict the passage of fluid present in the expandable driving member into the compartment 164 housing the drug units. Layer 176 further operates to essentially maintain the integrity of the drug units and the driving component 174. Layer 176 acts also to insure that the expanding driving force generated by the driving component is applied directly against the drug units. In operation, as the driving component 174 absorbs and imbibes fluid, it expands and pushes against layer 176, causing it to slide inside compartment 160. Layer 176 moves towards exit port 168, pushing the drug units through exit port 168 for maximizing the delivery of the drug to a biological environment of use, such as livestock.

Figure 10:
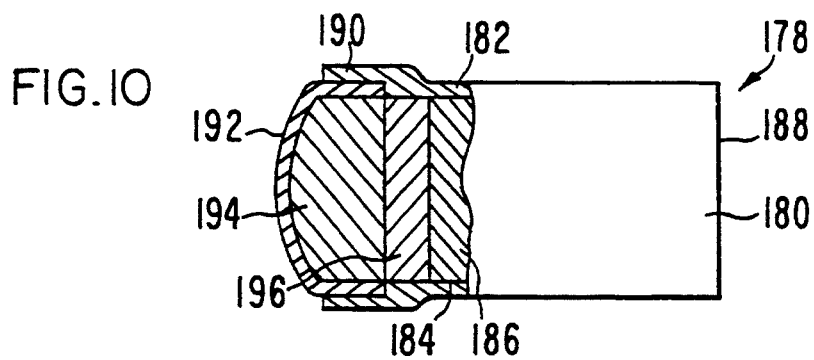
FIG. 10 is a partial cross-sectional view of another embodiment of the housing for the dispenser for this invention with means for releasably holding an insert member comprising an expandable member for pushing tablets out of the dispenser.

FIG. 10 is a partial cross-sectional view of another housing embodiment of delivery system 178 provided by the invention. In FIG. 10, delivery system 178 comprises housing member 180, wall 182 and internal compartment 184 that contains a plurality of drug units 186. In FIG. 10, wall 182 is continuous and it extends the length of delivery system 178. Wall 182 at its end distant from exit port 188 comprises a receiving end 190. Receiving end 190 is designed and adapted for receiving insert 192. Insert 192 is cup-like in shape, or tube-like with a single closed end, and it is made of a composition such as a polymeric composition that is permeable to the passage of an external fluid. Insert 192 comprises a driving component 194 and a layer or partition 196 that separates driving component 194 from the other ingredients present in compartment 184. Insert 192 in end 190, in a presently preferred embodiment, is replaceable and one or more than one insert 192 can be used during the operation of delivery system 178.

Figure 11:
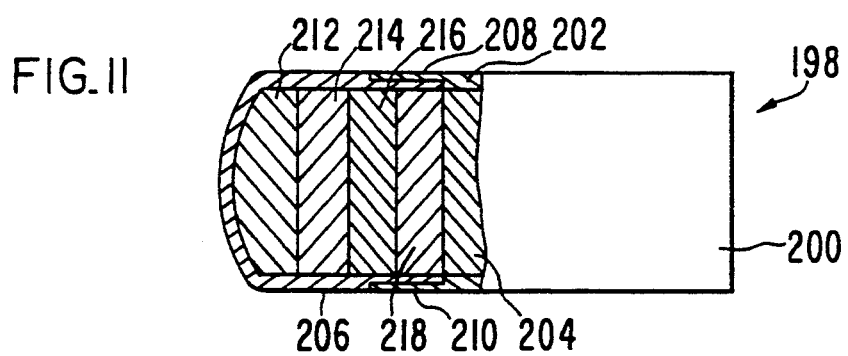
FIG. 11 is a partial cross-sectional view of still another embodiment of the housing having a first walled section and an engaging second walled section.

FIG. 11 is a partial cross-sectional view of delivery system 198 comprising housing member 200 formed by a first wall section 202 that surrounds an internal compartment area containing a plurality of drug units 204, and a second wall section 206 that surrounds an internal compartment area comprising at least one means for occupying space in the compartment. First wall section 202 is provided with receiving means 208. Wall 202 at receiving means 208 is thinner and it exhibits smaller internal dimensions for receiving second section 206 at its open end 210. Wall section 206 is thinner at its open end 210 and it exhibits smaller external dimensions for sliding into receiving end 208 in mated relation for providing an essentially continuous wall. The two sections can be joined together by various techniques such as solvent weld, adhesive bond, thermal weld, ultrasonic weld, spin weld, induction weld or by similar welding or bonding operations. First wall section 202 and second wall section 206 in the delivery system 198 seen in FIG. 11 are substantially uniform in cross-sectional dimensions, thereby providing delivery system 198 with substantially uniform dimensions along its central axis. In a presently preferred embodiment, delivery system 198 comprises a multiplicity of driving components 212, 214, and 216 which may comprise like or unlike compositions. Delivery system 198 in a presently preferred manufacture comprises layer 218 that separates the drug units 204 from the driving components.

Figure 12:
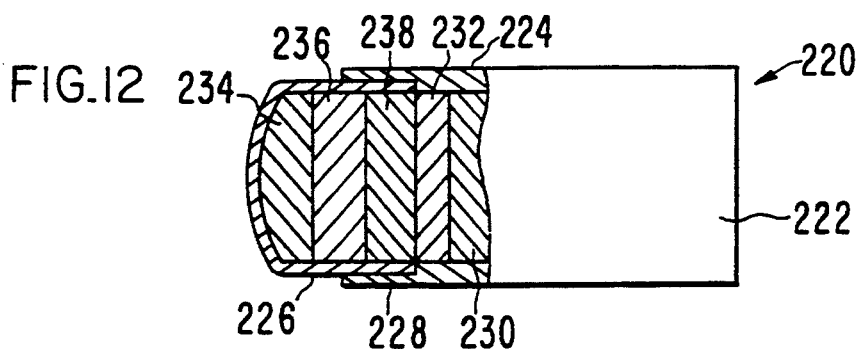
FIG. 12 is a partial cross-sectional view of another embodiment of the housing for the dispenser of this invention having a tablet-containing section and a driving force section joined as releasable engaging structural member sections.

FIG. 12 is a partial cross-sectional view of delivery system 220, which comprises housing member 222, first wall section 224, second wall section 226, receiving means 228, and a plurality of drug units 230. In FIG. 12, the first wall section 224 functions as a first body portion of delivery system 220 and it is designed for slipping over or for receiving second wall section 226, which serves as a second body portion. The second body portion is telescopically capped by the engaging first body portion 224. In FIG. 12, delivery system 220 comprises a partition 232 positioned near the drug units 230 contained within the space defined by first section 224, and at the filling entrance of second section 226 comprises a plurality of driving members 234, 236 and 238. The members are presently formed as depots or layers of the same or different member-forming compositions selected from the group consisting of the expandable materials disclosed herein.

Figure 13:
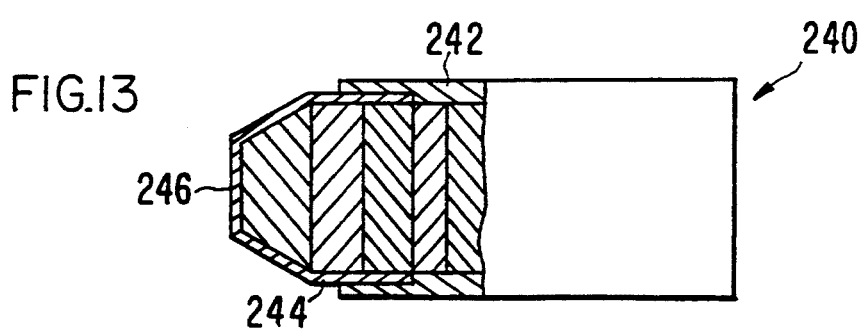
FIG. 13 is a partial cross-sectional view of still another embodiment of the housing where the end is tapered.
Figure 14:
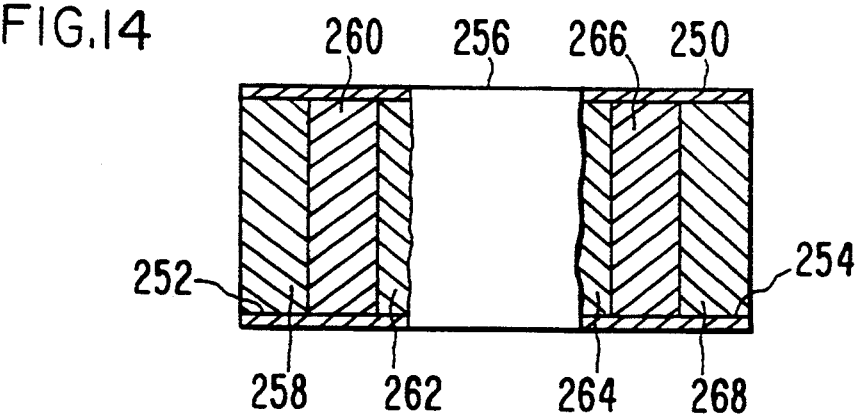
FIG. 14 is a partial cross-sectional view of the dispenser of this invention, illustrating another embodiment of the dispensing configuration.

In FIG. 13, a dosage form 240 is seen in cross-section, which dosage delivery form 240 is similar in structure and in operation to delivery form 220 illustrated in FIG. 12 and is comprised of a first wall section 242 and a second wall section 244. The second wall section 244 of the embodiment has a tapered end 246 rather than a dome-shaped end.

Another embodiment of the dispensing configuration is shown in FIG. 14, where multiple active agent units can be dispersed simultaneously or almost simultaneously. The dispenser of FIG. 14 is comprised of a rigid housing member 250 having two outlet means, exit ports 252 and 254, at opposite ends of the housing. A driving member 256 is present in the middle of housing 250 between exit ports 252 and 254. A plurality of movable discrete units 258, 260 and 262 are aligned within housing 250 between exit port 252 and driving member 256. A further plurality of movable discrete units 264, 266 and 268 are aligned within housing 250 between exit port 254 and driving member 256. This configuration is merely illustrative, and any number of units may be used in the dispenser.

The driving member 256 may be selected from those discussed previously herein; that is, it may include a fluid-swellable composition, an osmotically effective solute, or a gas-generating composition, for example. The driving member 256 when activated will displace units 258, 260 and 262 towards exit port 252, while at the same time displacing units 264, 266 and 268 towards exit port 254.

Figure 15:
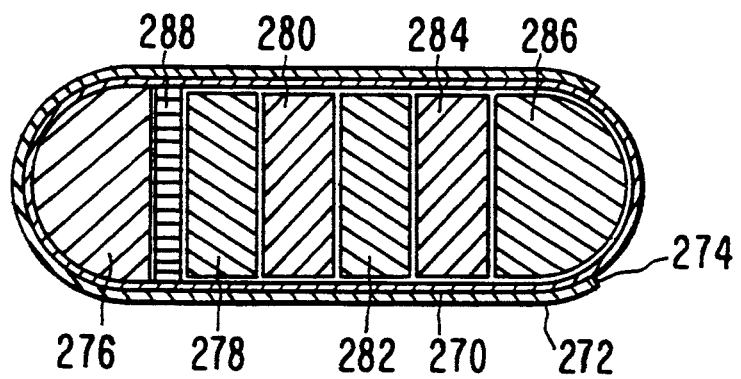
FIG. 15 is a cross-sectional view of the dispenser of this invention, illustrating another embodiment of the dispensing configuration and the housing.

FIG. 15 illustrates a further embodiment of the housing and the dispenser system of the invention. The system is comprised of a semipermeable rigid housing member 270 surrounded by a rate-controlling membrane 272 having an outlet means, exit port 274. A driving member 276 is present at the end of the housing 270 opposite from the exit port 274. A plurality of movable units 278, 280, 282, 284 and 286 are aligned within the housing 270 between exit port 274 and driving member 276. The units may be closely aligned, as illustrated, or they may be curved, as is shown in FIG. 2. The number of units shown is for illustrative purposes only, and any number of units may be used. The units may all contain drug, or drug-containing units may alternate with non-drug-containing units. An inert layer 288 may or may not be present to separate the driving member 276 from the drug units, 278 for example. Layer 288 is comparable to layer 176 in FIG. 9.

Semipermeable housing 270 is substantially permeable to external fluid and substantially impermeable to the ingredients contained in driving member 276 or in the drug units, 278 for example. The rate-controlling membrane 272 is selected from those membranes which will selectively allow passage of external fluid therethrough to the semipermeable housing 270 at a particular, predetermined rate. The membrane 272 will be substantially impermeable to any ingredients contained in driving member 276 or in the drug units, 278 for example.

Driving member 276 is typically a swellable material such as is described with reference to expandable member 78 in FIG. 4. When the dispenser is placed in the fluid environment, that portion of housing 270 not enclosed by the rate-controlling membrane 272, that is the area of the housing exposed to the environment at exit port 274, will dissolve, thus providing an open orifice at the exit port for passage of the drug units into the environment. The remaining housing 270 enclosed by rate-controlling membrane 272 will ultimately dissolve as well, as the fluid passes through membrane 272. However, such dissolution is relatively slower than that at the exit port, due to the presence of membrane 272. When the driving member 276 is activated by fluid passing through the rate-controlling membrane 272, it will displace the drug units sequentially towards and out exit port 274.

The amount of drug incorporated in the units of the dispenser of this invention varies widely depending on the particular drug, the desired therapeutic effect, and the time span for which it takes the drug to be released. Since a variety of units in a variety of sizes, shapes and compositions are intended to provide complete dosage regimes for therapy for a variety of maladies, there is no critical upper limit on the amount of drug incorporated in the units of the dispenser. The lower limit, too, will depend on the activity of the drug and the time span of its release from the units. Thus, it is not practical to define a range for the therapeutically effective amount of drug to be released by the individual units or by the dispenser as a whole.

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE II

A delivery system manufactured in the shape of a drug dispenser comprising a dispensing component with an exit port and a driving component is manufactured as follows. First, an expandable driving member is prepared by adding 9.5 liters of water and 500 g of polyvinylpyrrolidone to a stainless steel container and mixing the components for 20 hours to obtain a smooth binder solution. Next, 34.6 kg of sodium Carbomer ®, a sodium salt of polyacrylic acid polymer, is sized by forcing it through a 0.028 inch mesh screen in a fluid air mill set at 780–800 rpm speed. Then, 33 kg of the screened polymer is transferred to the granulator bowl of a fluid bed granulator, and 6.6 liters of the binder solution is slowly sprayed onto the polymer in the granulator. The polymer granules are formed in this manner.

Next, 15 kg of sodium chloride is milled in a mill to a number 21 size mesh screen. Then, 31.32 kg of the polymer granules of sodium Carbomer ® is mixed with 13.68 kg of the milled sodium chloride, and the mix is blended for about an hour. Then, 455 g of magnesium stearate is added and the ingredients are blended for 10 minutes to produce a homogeneous expandable driving composition. The composition next is pressed into osmotically active tablets in a tablet press at a pressure of 500 lbs to produce a round, flat-faced 30 mg tablet.

The driving component is comprised of a semipermeable wall that surrounds a compartment for containing the osmotically active tablet. This wall is prepared as follows. First, 3.85 kg of cellulose acetate butyrate and 1.15 kg of tributyl citrate are dry mixed in a mixer for 5 minutes. This produces a polymer plasticizer blend of a 77/23 ratio for the semipermeable wall. Next, a rubber mill is used to melt-blend the blend, at a roller temperature of 70° C. The blend is transferred to the moving rollers of the mill and mixed for 3 minutes. Then, after all the materials are added to the mill, the temperature is raised to 90° C., followed by milling for 2 minutes. Next, the temperature is raised to 115° C. and followed by two more minutes of milling, after which the temperature is increased to 133° C. and followed by six minutes of milling the blend, after which the temperature is increased to 144° C. and followed by six minutes of milling the blend. After the rollers are cooled to 50° C., the blend is removed from the mill. The milled blend is cut into strips and passed through a grinder mill, and the resulting particles are fed into an injection molder and molded into the semipermeable wall surrounding a compartment with an opened end for receiving an expandable driving member and for mating with the dispensing component of the delivery system.

Next, the dispensing component of the delivery system is prepared by adding 5 kg of polycarbonate to a hopper dryer and drying the polymer at 250° F. for 4 hours. The dry polymer is fed into the hopper of an injection molder, where a single-cavity hot-tip mold is used to injection-mold an impermeable wall surrounding a compartment with one open end for receiving the drug units and for mating with the semipermeable wall member, and a second open end which forms the exit port.

Next, the delivery system is assembled by first charging the subassembly (driving component) semipermeable walled member with three osmotic tablets. Then, microcrystalline wax is melted and the molten wax is poured on the top of the osmotic tablets to completely fill to the opened walled member. The charged subassembly is allowed to cool to room temperature.

Next, the delivery system subassembly (dispensing component) comprising the substantially impermeable wall surrounding the compartment is filled with a plurality of drug units in the form of compressed tablets, having the following composition: 90 wt % porcine somatotropin, 2 wt % polyvinylpyrrolidone, 1 wt % magnesium stearate, 3 wt % hydrogenated vegetable oil and 4 wt % histidine HCl. A suitable dosage of porcine somatotropin is about 112 mg per system. Therefore, the size and number of units will be designed accordingly. Then, the two subassemblies at their opened ends are joined by partially inserting the member comprising the osmotic tablets and the wax into the member comprising the drug units (layers). Next, 4 drops of moisture-cured cyanoacrylic adhesive are dropped into the remaining exposed surface, and the two members are fully inserted and twisted to effect a completed delivery system.

EXAMPLE III

A dispenser according to Example II is prepared. The drug unit composition is: 93 wt % porcine somatotropin, 2 wt % polyvinylpyrrolidone, 1 wt % magnesium stearate and 4 wt % histidine HCl. The hydrogenated vegetable oil is eliminated from the unit composition and, instead, about 50 μL of the vegetable oil is injected into the dispensing component. The dispensing component is then filled with the drug units and the subassemblies are joined as in Example II.

EXAMPLE IV

A dispenser according to Example II is prepared. When the dispensing component is being filled with the drug units, inert wax spacers are positioned alternating with the drug-containing units and the subassemblies are joined as in Example II.

EXAMPLE V

A delivery system in the shape of a drug dispenser generally according to FIG. 15, but without an inert layer 288, and containing gemfibrozil was manufactured as follows.

A swellable driving member was prepared as follows. 68.75 Weight percent Polyox® 303 (polyethylene oxide polymer), 5 wt % Carbopol® 934P (acidic carboxy polymer), 20 wt % sodium chloride, 5 wt % hydroxypropylmethylcellulose and 1 wt % red ferric oxide (for coloring) were first passed through a 40-mesh screen and then mixed in a Hobart® blender. After the mixture was mixed for 15 minutes, ethanol was slowly added (0.1 mL/gm). The resulting wet granulation was passed through a 20-mesh screen before air drying overnight at room temperature. The dried granulation was passed through a 20-mesh screen and blended with magnesium stearate for 5 to 10 minutes. The composition was pressed into round, flat-faced, osmotically active tablets of 150 mg weight each.

Each drug unit was prepared by mixing together 93.5 wt % gemfibrozil (Lopid®, a lipid regulating agent sold by Parke-Davis), 3.5 wt % hydroxypropylmethylcellulose, 2 wt % Ac-Di-Sol® (croscarmellose sodium) and 1 wt % magnesium stearate. The composition was pressed into drug units of 160 mg weight each.

An osmotically active tablet was placed in the end of one half of a size "0" hard gelatin capsule, after which three of the gemfibrozil drug units were added. A fourth drug unit was placed in the end of the other half of the capsule, and the capsule halves were joined together at their open ends, by inserting one half into the other, and then sealed.

The sealed capsule was then covered with a rate-controlling membrane of the composition: 70 wt % cellulose acetate 398-10, 15 wt % polyethylene glycol 3350 and 15 wt % Klucel® EF (hydroxypropylcellulose). The membrane was scraped away at the end containing the drug units, exposing a portion of the gelatin capsule, to give an exit port of approximately 156 mil diameter. The resulting gemfibrozil delivery system had a 65% drug loading.

The delivery system gave a mean drug release rate in vitro of between 35 mg/hr and 40 mg/hr between hours 4 and 16.

EXAMPLE VI

A dispenser according to Example V was prepared. The osmotically active tablet for the driving member had a weight of 250 mg and was composed of 68.5 wt % Polyox® 303, 10 wt % Carbopol® 934P, 15 wt % sodium chloride, 5 wt % hydroxypropylmethylcellulose, 1 wt % red ferric oxide and 0.5 wt % magnesium stearate.

The drug units were composed of 94 wt % gemfibrozil, 3.5 wt % hydroxypropylmethylcellulose, 2 wt % Ac-Di-Sol®, and 0.5 wt % magnesium stearate and weighed 128 mg each.

One osmotically active tablet and five drug units were placed in a size "00" hard gelatin capsule. The capsule was joined and sealed and coated with the rate-controlling membrane according to Example V, and an exit port was made with an orifice diameter of approximately 250 mil.

The mean release rate of the drug in vitro was 35.8 mg/hr between hours 4 and 16 (exit port pointing up).

EXAMPLE VII

Figure 16:
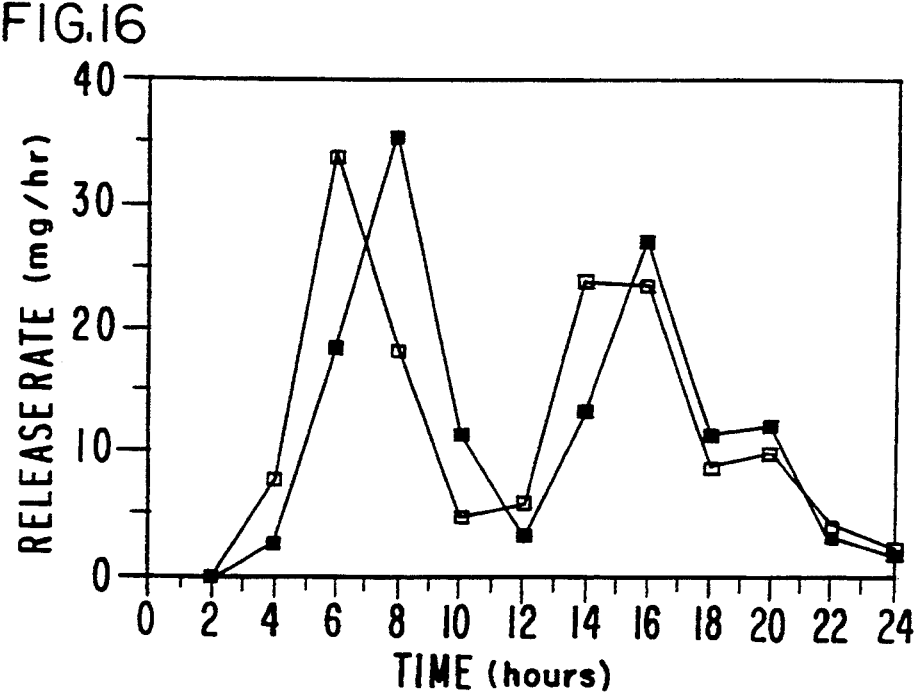
FIG. 16 shows the release rate for a two-pulse drug delivery device of the invention.

A dispenser according to Example V was prepared, except that two gemfibrozil drug units were alternated with two non-drug-containing units (blanks) in the capsule so that the initial unit to be released from the exit port was a blank, followed by a drug unit, a blank, and, lastly, a drug unit. This provided a two-pulse delivery system. The in vitro release rate of the system (with the exit port pointing up) is shown in FIG. 16.

The non-drug-containing units or blanks were composed of 93 wt % of Avicel® (microcrystalline cellulose), 5 wt % of hydroxypropylmethylcellulose and 2 wt % of Ac-Di-Sol®.

EXAMPLE VIII

A dispenser according to Example III is prepared, except that 95 wt % rather than 93 wt % of porcine somatotropin, and 2 wt % of copper sulfate rather than 4 wt % histidine HCl are included in the drug unit composition.

EXAMPLE IX

A delivery system in the shape of a drug dispenser generally according to FIG. 15, but without an inert layer 288, and containing flutamide was manufactured as follows.

Each drug unit was prepared as follows. Each of flutamide (80.0 wt %), cross-linked polyvinylpyrrolidone (13.5 wt %; Polyplasdone® XL-10), hydroxypropylmethylcellulose (4.0 wt %; "HPMC" 2910, 3 cps), and sodium lauryl sulfate (0.5 wt %) was first passed through a 40-mesh screen, and the components were then dry blended together in a Hobart mixer at low speed for 5 min. Purified water was then added slowly to the dry mixture while stirring until a wet mass was formed, after which the wet mass was passed through a 16-mesh screen and the resulting granules were air dried for 24 hr. The dried granules were then passed through a 16 mesh screen once again, and magnesium stearate, 80-mesh (2.0 wt %), was added and blended into the dried granulation by mixing in a roll mill for 5 min. The composition was pressed into drug units of 236 mg weight each.

A nondrug-containing unit was prepared by passing through a 40 mesh screen each of microcrystalline wax (80.0 wt %; Durawax® Microfine MF-2JH), kappa-carrageenan (15.0 wt %; colloid 710H, TIC) and HPMC (5.0 wt %; 2910, 5 cps). The excipients were then dry blended together in a Hobart mixer for 5 min at low speed. Anhydrous denatured ethanol was added to the dry mixture while the mixer was operating at low speed to give a wet mass, after which the resulting wet mass was passed through a 16 mesh screen and air dried for 24 hours. The dried granules were passed again through a 16 mesh screen. The composition was then pressed into non-drug units of 210 mg weight each.

A swellable driving member was prepared as follows. Kappa-carrageenan (68.0 wt %), polyvinylpyrrolidone (15.0 wt %; K 29–32), sorbitol (14.0 wt %), potassium chloride (1.0 wt %) and red ferric oxide (1.0 wt %) were first passed through a 40-mesh screen and then mixed in a Hobart mixer for 5 min at low speed. Anhydrous denatured ethanol was added slowly with the mixer operating on low speed until a wet mass was formed. The resulting wet mass was passed through a 16-mesh screen and then air dried for 24 hr. The dried granulation was passed through a 16-mesh screen and blended with magnesium stearate (1.0 wt %; 80-mesh) in a roll mill for 5 min. The composition was pressed into round osmotically active tablets of 170 mg weight each, the tablets having one flat face and one convex face.

To assemble a delivery system, an osmotically active tablet was placed in the end of one half of a size "0" hard gelatin capsule. One of the flutamide drug units was placed into the capsule above the osmotic tablet, followed by one non-drug unit and then a second flutamide unit. The capsule halves were joined together at their open ends and firmly closed.

The closed capsule was then coated with 55 mg of a semipermeable membrane having the composition: 60.0 wt % cellulose acetate and 40.0 wt % hydroxypropylcellulose (Klucel® EF). The membrane was applied from an 80:20 (w:w) acetone:methanol solvent mixture with a 4% solids content. Systems were coated in a Wurster® coater with a 6-in diameter column. A 0.275 inch drug release orifice was then cut in the drug-containing end of each system through the membrane and the gelatin. After solvent coating, the systems were air dried for 24 hr before testing.

EXAMPLE X

Devices from Example IX were tested in vitro for delivery of flutamide in two pulses, as follows.

Figure 17:
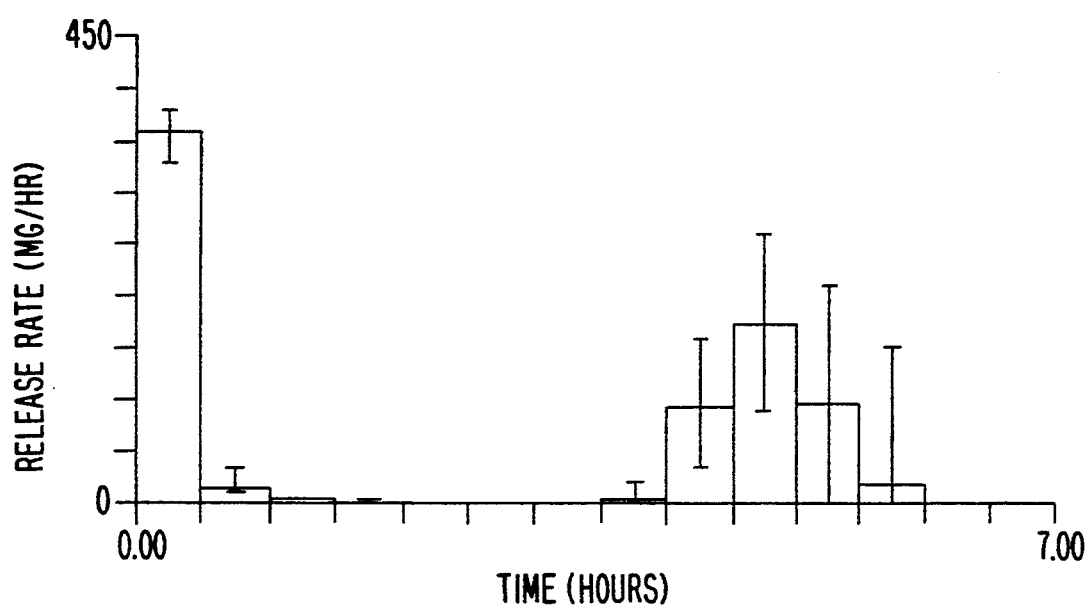
FIG. 17 shows the release rate for another two-pulse drug delivery device of the invention.

Ten devices were tested in a differential release tester. The devices were glued to rods and individually immersed for the first hour in artificial gastric fluid and thereafter in artificial intestinal fluid. Solution samples were obtained at half hour intervals. The flutamide release rate from the devices is shown in FIG. 17 (the bars represent min. and max.).

Devices according to Example IX were then tested in vivo in dogs in a feed-through experiment. It was discovered that, while the devices worked very well while in the gastric environment, those devices which had passed quickly through the stomach and entered the colon prior to the time of release of the second flutamide dosage did not in fact release the second dose. It was determined that the kappa-carrageenan osmotic driving member did not absorb sufficient fluid in the colon, which is a relatively low fluid-containing environment, to expand sufficiently to push the second flutamide drug unit from the device. However, when osmopolymers containing an osmagent (which gives increased fluid absorption characteristics to the polymer) were tested, it was found that these osmagent-containing driving members did not give a sharp, clean delivery of the second pulse of drug, apparently due to the fact that these driving members have a tendency to absorb onto or otherwise "stick" to the drug unit and not release the drug unit quickly or substantially completely within a short period of time into the fluid environment.

A solution to the problem of obtaining sharp pulsed release of active agent was found to be a bilayer fluid-activated osmotic driving means having 1) a first layer or member comprised of an osmotic material that absorbs sufficient fluid from a relatively low fluid-containing environment of use to expand to expel all of the drug units from the device, and 2) a second layer or member between the first osmotic member and the drug unit, adjacent to the drug unit, and comprised of an osmotic material that does not absorb onto or stick to the drug unit but expands to form a seal against the internal wall of the delivery device. The expansion of the second osmotic layer is desirable to form a seal to prevent seepage of the expanding first osmotic layer and thus to prevent contact of the first layer with the drug unit. An embodiment of the bilayer driving means is described in Example XI below.

EXAMPLE XI

A flutamide delivery device was prepared as in Example IX, except that two swellable osmotic driving members were prepared, as follows.

A first driving member was prepared following the procedures of Example IX but having the following composition: 58.5 wt % sodium carboxymethylcellulose, 35.0 wt % sodium chloride, 6.0 wt % HPMC, 0.25 wt % red ferric oxide and 0.25 wt % magnesium stearate. The composition was pressed into round osmotically active tablets of 220 mg weight each and having one flat face and one convex face.

A second driving member was prepared having the same composition as the driving member in Example IX. The composition was pressed into round osmotically active tablets of 30 mg weight each and having two flat faces.

To assemble the device, a first osmotic driving member tablet was placed into a size "0" extended gelatin capsule, followed by a second osmotic driving member tablet, a flutamide tablet, a nondrug-containing tablet and, finally, a second flutamide tablet. Assembly was continued following the procedures of Example IX.

EXAMPLE XII

A flutamide delivery device is prepared as in Example XI, except that kappa-carrageenan is used in place of the cross-linked polyvinylpyrrolidone in the drug units.

EXAMPLE XIII

A delivery device for the delivery of progesterone is prepared following the procedures of Example V. The osmotically active tablet for the driving member has a weight of 100 mg and is composed of 58.75 wt % sodium carboxymethylcellulose, 30 wt % sodium chloride, 5 wt % hydroxypropylmethylcellulose, 0.25 wt % magnesium stearate, 1 wt % red ferric oxide and 5 wt % Klucel EF®.

Two drug units are made, each drug unit weighing 143 mg and having a composition of 70 wt % micronized progesterone, 0.5 wt % magnesium stearate, 3 wt % hydroxypropylmethylcellulose, 3 wt % surfactant and 23.5 wt % Ac-Di-Sol®. Each unit contains 100 mg of progesterone.

One osmotically active tablet, followed by one drug unit are placed in a hard gelatin capsule. A non-drug-containing blank layer composed of 95 wt % stearic acid and 5 wt % hydroxypropylmethylcellulose is next placed in the capsule, followed by the second drug unit. The capsule is covered by 150 mg of a semipermeable membrane having a composition of 85 wt % cellulose acetate 398 and 15 wt % of polyethylene glycol 3350 and a large exit orifice is formed, to give a two-pulse delivery system.

The above pulsatile delivery device containing natural progesterone enables once daily dosing for treatment in hormone replacement therapy and secondary amenorrhea while avoiding undesirable side effects. Natural progesterone is used in treating abnormal bleeding and with estrogen for hormone replacement therapy for the menopausal woman. However, progesterone has poor systemic bioavailability when administered orally, due to extensive first pass metabolism. As such, it is currently marketed as an injectable or as an intrauterine contraceptive. A single oral dose administration (i.e., bolus administration) of progesterone in an amount of from about 125 mg to about 300 mg delivered as a bolus and sufficient to provide the desired plasma levels for a therapeutically effective response over 24 hours has been found to also give a potentially greater incidence of undesirable side effects such as somnolence, while a divided dose regimen of morning and evening oral bolus administrations at lower doses has been shown to avoid the potential side effects (Sitruk-Ware, R., et al., *Contraception* 36:373–402 (1987)). However, twice-daily dosing has certain disadvantages such as the fact that it creates a greater probability of lack of compliance in that it is more inconvenient and easier to forget to take a pill twice a day rather than just once. The pulsatile device of the present invention alleviates the disadvantages of both of these administrative regimens by providing a once-daily dosing regimen that delivers an amount of progesterone twice during a 24 hour period, each dose being of from about 50 mg to about 100 mg, to provide a therapeutic effect while avoiding the potential side effects attendant with the prior art once-daily bolus administration. Additionally, it enables sufficient dosage to maintain the desired efficacy while avoiding a constant first pass effect.

The pulsatile device of the present invention is useful as well in delivering other drugs which exhibit a significant or extensive first pass effect. By "significant or extensive first pass effect" is meant that at least about 35%, preferably at least about 45%, of the drug is inactivated by the liver on the first-pass. Such drugs are known in the art or can be determined by reference to the medical or pharmaceutical literature, such as *The Merck Index and Remington's Pharmaceutical Sciences*, for example. Such drugs include, but are not limited to, drugs such as melatonin, propranolol and verapamil.

EXAMPLE XIV

A non-pulsatile, extended delivery (i.e., zero-order rather than bolus) progesterone device is prepared following the procedures of Example XIII, except that no nondrug-containing blank layer is placed between the two drug units and the composition of each drug unit is: 80 wt % micronized progesterone, 0.5 wt % magnesium stearate, 3 wt % hydroxypropylmethylcellulose, 3 wt % surfactant and 13.5 wt % Ac-Di-Sol ®. Each unit weighs 125 mg and contains 100 mg of progesterone.

The above device for delivering natural progesterone over an extended period of time of up to from about 10 hours to about 24 hours enables once daily dosing for treatment in hormone replacement therapy and secondary amenorrhea to provide a therapeutic effect while avoiding the potential undesirable side effects attendant with the prior art once-daily bolus administration.

EXAMPLE XV

A device is prepared, following the general procedure of Example XIII, for delivering melatonin to a mammal following a predetermined initial delay after administration of the device, to simulate the natural circadian rhythmic profile of melatonin in mammals, wherein the device contains an osmotically active tablet, two drug-containing units comprising melatonin, and one nondrug-containing unit. The non-drug unit is placed adjacent the outlet orifice of the device and the melatonin-containing units are placed between the non-drug unit and the osmotically active tablet.

The drug-containing units together comprise melatonin in an amount and together with additives to give a formulation which provides a delivery of melatonin in an amount which provides a plasma level of from about 20 pg/mL to 1,000 pg/mL of melatonin over a period of about 4 to 6 hours.

The nondrug-containing unit is sized such that delivery of the nondrug-containing unit and the drug-containing units from the device to the mammal environment provides a delay for a predetermined period of time after administration of the device to the mammal, after which delay the delivery of melatonin begins.

This invention has been described in detail with particular reference to certain preferred embodiments thereof, but it will be understood that variations and modifications can be effected within the spirit and scope of the invention.

We claim:

1. A dispenser for the delivery to a fluid-containing environment of a drug which exhibits a significant or extensive first pass effect, the dispenser comprising, in combination:
   a. a rigid housing open at one end to provide outlet means therefor, at least a portion of said housing proximate the end of said housing opposite the outlet means permitting passage of the fluid in said environment to the interior of said housing;
   b. a fluid-activated driving means within said housing in fluid-transmitting relationship with the fluid-passing portion of said housing proximate the end of said housing opposite said outlet means, said driving means, upon exposure of said dispenser to said fluid environment, being the source of motive power for moving the contents of said housing through said outlet means; and
   c. a plurality of solid, discrete dosage units comprising a drug which exhibits a significant or extensive first pass effect longitudinally disposed within said housing between said driving means and said outlet means, whereby said drug units will be sequentially displaced from said housing into said fluid environment by said driving means upon exposure of said dispenser to said fluid environment.

2. A dispenser according to claim 1 wherein said drug units are separated by nondrug-containing units.

3. A dispenser for the delivery of progesterone to a fluid-containing environment, the dispenser comprising, in combination:
   a. a rigid housing open at one end to provide outlet means therefor, at least a portion of said housing proximate the end of said housing opposite the outlet means permitting passage of the fluid in said environment to the interior of said housing;
   b. a fluid-activated driving means within said housing in fluid-transmitting relationship with the fluid-passing portion of said housing proximate the end of said housing opposite said outlet means, said driving means, upon exposure of said dispenser to said fluid environment, being the source of motive power for moving the contents of said housing through said outlet means; and c. a plurality of solid, discrete dosage units comprising progesterone longitudinally disposed within said housing between said driving means and said outlet means, whereby said progesterone units will be sequentially displaced from said housing into said fluid environment by said driving means upon exposure of said dispenser to said fluid environment.

4. A dispenser according to claim 3 wherein said progesterone is micronized progesterone.

5. A dispenser according to claim 3 wherein said progesterone units are separated by nondrug-containing units.

6. A dispenser according to claim 5 which comprises two progesterone units separated by one nondrug-containing unit.

7. A dispenser according to claim 3 wherein said driving means comprises an osmopolymer, an osmagent or a mixture of an osmagent in an osmopolymer.

8. A method for providing delivery to a fluid-containing environment of a drug selected from the group consisting of flutamide, phenytoin and drugs which exhibit a significant or extensive first pass effect, the method comprising the steps of:

1) placing in said environment a dispenser comprising, in combination:
   a. a rigid housing open at one end to provide outlet means therefor, at least a portion of said housing proximate the end of said housing opposite the outlet means permitting passage of the fluid in said environment to the interior of said housing;
   b. a fluid-activated driving means within said housing in fluid-transmitting relationship with the fluid-passing portion of said housing proximate the end of said housing opposite said outlet means, said driving means, upon exposure of said dispenser to said fluid environment, being the source of motive power for moving the contents of said housing through said outlet means; and
   c. a plurality of solid, discrete dosage units comprising said drug longitudinally disposed within said housing between said driving means and said outlet means; and 2) allowing fluid to be imbibed through said housing of said dispenser for causing said driving means to expand to sequentially displace said drug units from said housing into said fluid environment.

9. A method according to claim 8 wherein said drug units are separated by nondrug-containing units to provide a pulsatile delivery to said fluid environment.

10. A method according to claim 9 wherein said dispenser comprises two drug units separated by one nondrug-containing unit, and the drug is flutamide.

11. A method according to claim 9 wherein said dispenser comprises two drug units separated by one nondrug-containing unit, and the drug is progesterone.

12. A method according to claim 11 wherein said progesterone is micronized progesterone.

13. A method according to claim 8 wherein said driving means comprises an osmopolymer, an osmagent or a mixture of an osmagent in an osmopolymer.

14. A method for maintaining a therapeutically effective plasma level of progesterone in a mammal while decreasing side effects attendant with the once-daily bolus administration of progesterone in an amount of from about 125 mg to about 300 mg, wherein the method comprises administering orally once daily to said mammal said progesterone from a dosage form which delivers two pulses of said progesterone in an amount of about 50 mg to about 100 mg each.

15. A method according to claim 14 wherein said dosage form is a dispenser, said dispenser comprising:
   a. a rigid housing open at one end to provide outlet means therefor, at least a portion of said housing proximate the end of said housing opposite the outlet means permitting passage of the fluid in said environment to the interior of said housing;
   b. a fluid-activated driving means within said housing in fluid-transmitting relationship with the fluid-passing portion of said housing proximate the end of said housing opposite said outlet means, said driving means, upon exposure of said dispenser to said fluid environment, being the source of motive power for moving the contents of said housing through said outlet means; and
   c. two solid, discrete dosage units comprising progesterone, each dosage unit comprising from about 50 mg to about 100 mg of progesterone, said dosage units being longitudinally disposed within said housing between said driving means and said outlet means, said dosage units being separated by a nondrug-containing unit, whereby said dosage units will be sequentially displaced from said housing into said fluid environment by said driving means upon exposure of said dispenser to said fluid environment.

16. A method according to claim 15 wherein said progesterone is micronized progesterone.

17. A method according to claim 15 wherein said driving means comprises an osmopolymer, an osmagent or a mixture of an osmagent in an osmopolymer.

18. A method for maintaining a therapeutically effective plasma level of progesterone in a mammal while decreasing side effects attendant with the once-daily bolus administration of progesterone in an amount of from about 125 mg to about 300 mg, wherein the method comprises administering orally once daily to said mammal said progesterone in a dosage form which delivers said progesterone in a total amount of about 125 mg to about 300 mg over an extended period of time of from about 10 hours to about 24 hours.

19. A method according to claim 18 wherein said dosage form is a dispenser, said dispenser comprising:
   a. a rigid housing open at one end to provide outlet means therefor, at least a portion of said housing proximate the end of said housing opposite the outlet means permitting passage of the fluid in said environment to the interior of said housing;
   b. a fluid-activated driving means Within said housing in fluid-transmitting relationship with the fluid-passing portion of said housing proximate the end of said housing opposite said outlet means, said driving means, upon exposure of said dispenser to said fluid environment, being the source of motive power for moving the contents of said housing through said outlet means; and
   c. a plurality of solid, discrete dosage units comprising progesterone, said dosage units being longitudinally disposed within said housing between said driving means and said outlet means, whereby said dosage units will be sequentially displaced from said housing into said fluid environment by said driving means upon exposure of said dispenser to said fluid environment.

20. A method according to claim 19 wherein said progesterone is micronized progesterone.

21. A method according to claim 19 wherein said driving means comprises an osmopolymer, an osmagent or a mixture of an osmagent in an osmopolymer.

* * * * *